United States Patent [19]

Moshchitsky et al.

[11] Patent Number: 5,262,541
[45] Date of Patent: Nov. 16, 1993

[54] FLUORENOL CATALYZED REDUCTION OF O-NITROAZOBENZENES AND 2-ARYL-2H-BENZOTRIAZOLE-N-OXIDES

[75] Inventors: Semyon Moshchitsky, Old Bridge, N.J.; William E. Leistner, Atlantic Beach, N.Y.; Howard R. Leistner, Tibron, Calif.

[73] Assignee: Fairmont Chemical Company, Inc., Newark, N.J.

[21] Appl. No.: 990,694

[22] Filed: Dec. 15, 1992

[51] Int. Cl.$^5$ .............................. C07D 249/20
[52] U.S. Cl. ..................... 548/260; 548/259
[58] Field of Search ................. 548/259, 260

[56] References Cited

U.S. PATENT DOCUMENTS

| | | | |
|---|---|---|---|
| 2,362,988 | 11/1944 | Conzetti | 260/308 |
| 3,773,751 | 11/1973 | Brooks, Jr. | 260/206 |
| 4,642,350 | 2/1987 | Davitz et al. | 548/260 |
| 4,780,541 | 10/1988 | Seino | 548/260 |
| 4,835,284 | 5/1989 | Seino | 548/259 |

FOREIGN PATENT DOCUMENTS 0257151  3/1986  European Pat. Off.

*Primary Examiner*—Patricia L. Morris
*Attorney, Agent, or Firm*—Richard S. Roberts

[57] ABSTRACT

A process for producing 2-aryl-2H-benzotriazole by reducing an o-nitroazobenzene with a saccharide having an aldehyde group as a reducing agent in the presence of fluorenol as a catalyst and a base in solution. The reaction is conducted at a temperature of from about 60° C. to about 80° C. The reaction time and amount of catalyst is significantly reduced compared to the use of an aromatic ketone catalyst. The invention also provides a method for producing 2-aryl-2H-benzotriazole by reducing a 2-aryl-2H-benzotriazole-N-oxide intermediate with a saccharide having an aldehyde group as a reducing agent, in the presence of fluorenol under similar conditions.

22 Claims, No Drawings

FLUORENOL CATALYZED REDUCTION OF O-NITROAZOBENZENES AND 2-ARYL-2H-BENZOTRIAZOLE-N-OXIDES

BACKGROUND OF THE INVENTION

The present invention relates to a method for the production of 2-aryl-2H-benzotriazoles by the catalytic reduction of o-nitroazobenzenes or intermediate 2-aryl-2H-benzotriazole-N-oxides. The reduction is performed with a saccharide having an aldehyde group as a reducing agent, in the presence of fluorenol as a catalyst and a base in an aqueous alcoholic solution.

2-Aryl-2H-benzotriazoles are known in the art as ultraviolet absorbing compounds useful for paints, plastics, coatings and the like, and 2-aryl-2H-benzotriazole-N-oxides are useful as intermediates for the production of 2-aryl-2H-benzotriazoles.

It is known in the art that 2-aryl-2H-benzotriazoles such as 2-phenylbenzotriazole may be produced by reducing o-nitroazobenzenes through a 2-phenylbenzotriazole-N-oxide intermediate. A wide variety of reduction techniques is known. Reduction of o-nitroazobenzenes to 2-phenylbenzotriazole by zinc in the presence of sodium hydroxide is disclosed in U.S. Pat. Nos. 3,018,269; 3,230,194; 3,773,751; 4,041,044; and 4,224,451, among others. However, this method is disadvantageous since the disposal of zinc sludge poses a significant environmental problem. The presence of residues of zinc in the benzotriazole product is detrimental to the ageing of some polymers.

Reduction with sodium hydrosulfite, sodium sulfide or sodium bisulfite are known from DE 3,731,860; EPA 130,938, and Swiss patent 660,591. Reduction by thiourea S,S-dioxide is disclosed in Japanese Kokai 61-218,577 and SU 1,159,920.

Reduction by carbon monoxide is shown in U.S. Pat. No. 4,141,903 and German Offenlegungsschrift 2,835,846. These latter processes are not preferred since they give a poor yield and are not economical.

Electrochemical reduction is disclosed in Japanese Kokai 63-186,886.

Several hydrogenation techniques are shown in German Offenlegungsschrifts 2,455,155; 2,620,970, and 2,620,897; Japanese Kokais 77-113,974 and 01-71,862; Swiss patents 615,165; 615,166 and 615,167; Canadian patents 1,154,778; 1,154,779; and European patent applications EP 380,839 and 380,840. Hydrogenation processes are carried out in an aqueous alkaline medium in the presence of finely divided platinum, nickel, palladium, rhodium or ruthenium. In hydrogenation reactions the metal catalyst serves to absorb hydrogen molecules on its surface. This absorption of hydrogen is essentially a chemical reaction where unpaired electrons on the surface of the metal mate with the electrons of hydrogen and bind the hydrogen to the surface. The collision of the nitro group from the azo-dye with the surface having absorbed hydrogen causes absorption of the nitro group as well. A step wise transfer of hydrogen atoms takes place and this produces an N-Oxide of hydroxylamine, which immediately cyclizes with the azo group and forms the N-oxide of benzotriazole. This N-oxide under the same mechanism is converted to the corresponding benzotriazole. Other reduction methods are disclosed in German Offenlegungsschrifts 2,551,853 and 2,835,529; Japanese Kokais 59-170,172; 59-172,481; 02-202,878; 02-273,677 and 02-202,877; as well as European EP 160,246.

Reduction using aldehyde reducing agents and aromatic ketone catalysts is disclosed in U.S. Pat. No. 4,835,284. Reduction using saccharides and an aromatic ketone catalyst is disclosed in U.S. Pat. Nos. 4,780,541 as well as European patent application 0,257,151. These show methods for the preparation of benzotriazoles by reductive cyclization of azo dyes with saccharides in the presence of aromatic ketone catalysts, which act by receiving hydrogen from the reducing agent and giving hydrogen to a material to be reduced. In each of these cases, saccharide reduction is catalyzed by such aromatic ketone catalysts as substituted and unsubstituted fluorenone, benzanthrone, hydroquinone, naphthoquinone, diphenoquinone, anthrone, phenanthrenequinone, anthraquinone, benzophenone, xanthenone, and the like. A disadvantage of this method is that the time of the reduction reaction and the amount of ketone catalyst is very much greater than that required for the present invention. Each of the above disclosures are incorporated herein by reference.

It has now been unexpectedly found that when reduction is done with a saccharide having an aldehyde group as a reducing agent, and fluorenol as the hydrogen transfer catalyst, which gives hydrogen to the material to be reduced and then takes hydrogen from a glucose reducing agent, that the reaction proceeds much more quickly and the amount of fluorenol required is much less compared to the use of ketone catalysts. Although the prior art shows the use of the aromatic ketone-fluorenone as a catalyst, the use of corresponding aromatic alcohol-fluorenol shows much improved results in comparison. The use of fluorenol is unique because this improvement is not apparent when other aromatic alcohols are used.

SUMMARY OF THE INVENTION

The invention provides a method for the production of 2-aryl-2H-benzotriazoles which comprises reducing an o-nitroazobenzene compound with a saccharide having an aldehyde group as a reducing agent, in the presence of fluorenol as a catalyst, and a base in an aqueous alcoholic solution, at a temperature of from about 60° C. to about 80° C., for a sufficient time and under conditions sufficient to produce 2-aryl-2H-benzotriazole. The invention also provides a method for the production of 2-aryl-2H-benzotriazole which comprises reducing a 2-aryl-2H-benzotriazole-N-oxide compound with a saccharide having an aldehyde group as a reducing agent, in the presence of fluorenol as a catalyst, and a base in an aqueous alcoholic solution, at a temperature of from about 60° C. to about 80° C., for a sufficient time and under conditions sufficient to produce 2-aryl-2H-benzotriazole.

DETAILED DESCRIPTION OF THE PREFERRED EMBODIMENT

The invention provides a method for preparing 2-aryl-2H-benzotriazoles and in particular 2-phenylbenzotriazoles having the general formula I:

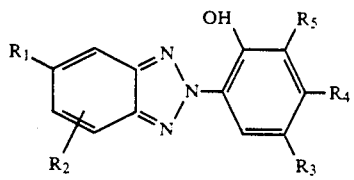

wherein $R_1$ represents hydrogen or chlorine atom, a lower alkyl group having a carbon number of 1 to 4, a lower alkoxyl group having a carbon number of 1 to 4, carboxyl group, or sulfonic acid group; $R_2$ represents hydrogen or chlorine atom, a lower alkyl group having a carbon number of 1 to 4, or a lower alkoxyl group having a carbon number of 1 to 4; $R_3$ represents hydrogen or a halogen atom, preferably a chlorine atom, an alkyl group having a carbon number of 1 to 12, a lower alkoxyl group having a carbon number of 1 to 4, phenyl group, a phenyl group substituted with an alkyl group having a carbon number of 1 to 8, phenoxy group, or a phenylalkyl group, the alkyl part of which has a carbon number of 1 to 4; $R_4$ represents hydrogen or chlorine atom, hydroxyl group, or a lower alkoxyl group having a carbon number of 1 to 4; and $R_5$ represents hydrogen atom, an alkyl group having a carbon number of 1 to 12, or a phenylalkyl group, the alkyl part of which has a carbon number of 1 to 4. This is done by reducing o-nitroazobenzenes having the general formula II:

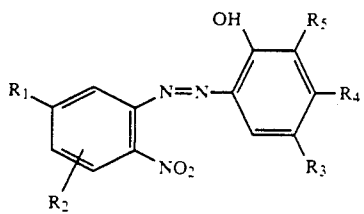

wherein $R_1$, $R_2$, $R_3$, $R_4$ and $R_5$ are as defined above, with a saccharide having an aldehyde group as a reducing agent in the presence of fluorenol as a catalyst, and a base in an aqueous alcoholic solution. The invention also provides a method for preparing 2-aryl-2H-benzotriazoles, in particular, 2-phenylbenzotriazoles having the above formula I by reducing 2-phenylbenzotriazole-N-oxides having the general formula III:

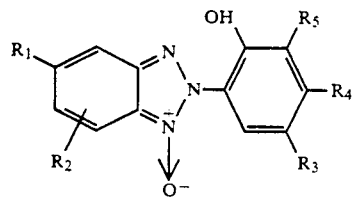

wherein $R_1$, $R_2$, $R_3$, $R_4$ and $R_5$ are the same as defined above with a saccharide having an aldehyde group as a reducing agent, in the presence of fluorenol as catalyst, and a base in an aqueous alcoholic solution. In the preferred embodiment, $R_1$, $R_2$, $R_4$ and $R_5$ are hydrogen, and $R_3$ is a $C_1$-$C_{12}$ alkyl group or a halogen atom. In the most preferred embodiment, $R_1$, $R_2$, $R_4$ and $R_5$ are hydrogen, and $R_3$ is methyl or t-octyl.

In the practice of the present invention, a method is prepared which is broadly provides for the reduction of an o-nitroazobenzene with a saccharide having an aldehyde group as a reducing agent, preferably glucose, in the presence of fluorenol as a catalyst, and a base in solution to produce 2-aryl-2H-benzotriazole.

The o-nitroazobenzene component is an azo dyestuff and the amounts of all of the other reaction components are present with reference to it. The o-nitroazobenzenes used in the present invention can be prepared by diazotizing o-nitroanilines, according to the method described in U.S. Pat. No. 4,780,541 which is incorporated herein by reference. Examples of o-nitroazobenzenes non-exclusively include:
2-nitro-2'-hydroxy-5'-methylazobenzene,
2-nitro-2'-hydroxy-5'-t-octylazobenzene,
2-nitro-2'-hydroxy-5'-t-butylazobenzene,
2-nitro-2',4'-dihydroxyazobenzene,
2-nitro-4-chloro-2',4'-dihydroxyazobenzene,
2-nitro-2'-hydroxy-4'-methoxyazobenzene,
2-nitro-2'-hydroxy-5'-t-amylazobenzene,
2-nitro-4'-chloro-2'-hydroxy-5'-t-amylazobenzene,
2-nitro-2'-hydroxy-5'-n-dodecylazobenzene,
2-nitro-4-chloro-2'-hydroxy-5'-n-dodecylazobenzene,
2-nitro-4-chloro-2'-hydroxy-5'-t-octylazobenzene,
2-nitro-4-methyl-2'-hydroxy-5'-methylazobenzene,
2-nitro-4,6-dichloro-2'-hydroxy-5'-t-butylazobenzene, and 2-nitro-4-carboxy-2'-hydroxy-5-methylazobenzene.

In another aspect of the invention, the N-oxide intermediates may be used as starting materials for the production of the benzotriazoles. Examples of 2-phenylbenzotriazole-N-oxides used in the method of the present invention include:
2-(2-hydroxy-5-methylphenyl)benzotriazole-N-oxide,
2-(2-hydroxy-5-t-butylphenyl)benzotriazole-N-oxide,
2-(2-hydroxy-5-t-octylphenyl)benzotriazole-N-oxide,
2-(2,4-dihydroxyphenyl)benzotriazole-N-oxide,
2-(2,4'-dihydroxyphenyl)-5-chlorobenzotriazole-N-oxide,
2-(2-hydroxy-4'-methoxyphenyl)benzotriazole-N-oxide,
2-(2-hydroxy-5-t-amylphenyl)benzotriazole-N-oxide,
2-(2-hydroxy-5-n-dodecylphenyl)benzotriazole-N-oxide,
2-(2-hydroxy-5-n-dodecylphenyl)-5-chlorobenzotriazole-N-oxide,
2-(2-hydroxy-5-t-octylphenyl)-5-chlorobenzotriazole-N-oxide,
2-(2-hydroxy-5-methylphenyl)-5-methylbenzotriazole-N-oxide,
2-(2-hydroxy-5-methylphenyl)-5-carboxybenzotriazole-N-oxide,
2-(2-hydroxy-3-t-butyl-5-methylphenyl)-5-chlorobenzotriazole-N-oxide,
2-(2-hydroxy-3,5-di-t-butylphenyl)-5-chlorobenzotriazole-N-oxide,
2-(2-hydroxy-3,5-di-t-amylphenyl)benzotriazole-N-oxide,
2-(2-hydroxy-3,5'-di-t-butylphenyl)benzotriazole-N-oxide,
2-(2-hydroxy-3-t-butyl-5-methylphenyl)benzotriazole-N-oxide,
2-(2-hydroxy-3,5'-di-t-octylphenyl)benzotriazole-N-oxide,
2-(2-hydroxy-3,5'-di-t-octylphenyl)-5-chlorobenzotriazole-N-oxide,
2-(2-hydroxy-3-t-butyl-5-methylphenyl)-5-methylbenzotriazole-N-oxide, 2-(2-hydroxy-3,5'-di-t-butylphenyl)-5-n-butylbenzotriazole-N-oxide, 2-(2-hydroxy-3-sec-butyl-5-t-butylphenyl)-5-n-butylbenzotriazole-N-oxide, 2-(2-hydroxy-3-sec-butyl-5-t-butylphenyl)-5-t-butylbenzotriazole-N-oxide, 2-(2-hydroxy-3,5-di-t-butylphenyl)-5,7-dichlorobenzotriazole-N-oxide, 2-(2-hydroxy-3,5-di-t-amylphenyl)-5-chlorobenzotriazole-N-oxide, 2-[2-hydroxy-3,5-di-(alpha,alpha-dimethylbenzyl)-phenyl]benzotriazole-N-oxide, 2-[2-hydroxy-3,5-di-(alpha,alpha-dimethylbenzyl)-phenyl]-5-chlorobenzotriazole-N-oxide, 2-(2-hydroxy-3-alpha-methylbenzyl-5-methylphenyl)-benzotriazole-N-oxide, and 2-(2-hydroxy-3-alpha-methylbenzyl-5-methylphenyl)-5-chlorobenzotriazole-N-oxide.

The method employs a saccharide having an aldehyde group as a reducing agent. Examples of such saccharides non-exclusively include glucose, fructose, sucrose, lactose and maltose. The saccharide component is preferably present in an amount of at least 2 mols per mol of o-nitroazobenzene or more preferably from about 2 to about 4 mols per mol of o-nitroazobenzene and most preferably about 3 mols. When the N-oxide is used as the starting material, approximately one half these amounts of saccharide are required.

The method employs fluorenol as a catalyst. Fluorenol is preferably present in an amount of from about 1.5% to about 10% by weight of the o-nitroazobenzene, more preferably from about 2% to about 2.5%. Approximately one half of these amounts are required when the N-oxide is selected as the starting material.

The reaction takes place in a suitable medium which is conducive to productively conducting the process. In the most preferred embodiment, the medium is water in admixture with a water miscible, lower alkyl alcohol, preferably a $C_1$-$C_4$ alcohol. The most preferred alcohols are methanol, ethanol, isopropanol, n-propanol, and t-butanol. The alcohol is present in an amount of from about 100% to about 500%, and preferably from about 140% to about 160% based on the weight of the o-nitroazobenzene or N-oxide. The entire medium is used in the reaction in an amount sufficient to drive the reaction and preferably from about 200% to about 800% or more preferably from about 300% to about 350% based on the weight of the o-nitroazobenzene or N-oxide.

The reaction proceeds in the presence of a base which may include hydroxides such as alkali metal and alkaline earth metal hydroxides. The most preferred hydroxides are sodium hydroxide, potassium hydroxide and lithium hydroxide. The amount of hydroxide is preferably from about 60% to about 200%, or more preferably from about 90% to about 100% based on the weight of the o-nitroazobenzene or N-oxide.

In the preferred embodiment, the reduction is conducted for from about 2 hours to about 6 hours, or more preferably from about 2 hours to about 4 hours depending on the selection of o-nitroazobenzene or N-oxide. The most advantageous reaction time may be determined by those skilled in the art.

In the preferred embodiment, the reduction is conducted at a temperature of from about 60° C. to about 80° C., or more preferably from about 70° C. to about 75° C.

The reaction is conducted in a single kettle batch reaction by mixing the relevant amounts of each component with the requisite stirring and heating particular to the materials employed.

The following non-limiting examples serve to illustrate the invention.

EXAMPLE 1

2-(2'H-Benzotriazol-2'-yl)-4-tert-octylphenol (TTA)

35.5 g (0.1 mole) of 2-nitro-2'-hydroxy-5-t-octylazobenzene are added to the mixture of 60 ml of methanol, 0.7 g of fluorenol and 4 g of 50% aqueous solution of sodium hydroxide. The mixture is stirred at 70°–75° C. and to the mixture is slowly added 55.4 g (0.3 mol) of glucose in 55 ml of water over 1 hour. The reaction mixture is heated for an additional hour, then 160 ml of methanol is added at 55°–60° C. and 14.2 g of 35% hydrochloric acid slowly added and stirred at 40°–50° C. for 20 minutes. During this time crystals should appear. Then more hydrochloric acid is added to attain pH 4–5. The reaction is cooled to 25° C. to yield 29.1 g of product (90%). mp 103°–104° C.

EXAMPLE 2

Example 1 is repeated except the conditions in the following table are used and the indicated result obtained. In these cases either o-nitroazobenzenes (azo-dyes) or the intermediate 2-aryl-2H-benzotriazole-N-oxides are used to obtain 2-aryl-2H-benzotriazoles.

| Starting Material | Fluorenol Concent. % Weight | Reaction Time Hrs. | Reaction Temp. °C. | Glucose mol/mol | Yield of Crude Prod. % | Product Quality by TLC | Product Quality by HPLC % |
|---|---|---|---|---|---|---|---|
| N-Oxide | 5 | 2 | 70–72 | 2 | 94.0 | Pure TTA | — |
| N-Oxide | 2.6 | 2 | 75 | 2 | 80.0 | Pure TTA | — |
| N-Oxide | 2.5 | 3 | 75 | 2 | 96.4 | Puur TTA | — |
| N-Oxide | 1.0 | 3 | 75 | 2 | 84.9 | Contaminated by N-Oxide | — |
| N-Oxide | 1.0 | 3 | 75 | 2 | 90.4 | Contaminated by N-Oxide | Assay-68 N-oxide 29 |
| N-Oxide | 0.5 | 3 | 75 | 2 | 85.2 | Contaminated by N-Oxide | Assay-66 N-oxide 31 |
| Azo-Dye | 5 | 2 | 70–74 | 2 | 76.4 | Pure TTA | — |
| Azo-Dye | 2.5 | 4 | 75 | 3 | 86.0 | Pure TTA | Assay-90 N-Oxide |

-continued

| Starting Material | Fluorenol Concent. % Weight | Reaction Time Hrs. | Reaction Temp. °C. | Glucose mol/mol | Yield of Crude Prod. % | Product Quality by TLC | Product Quality by HPLC % |
|---|---|---|---|---|---|---|---|
| Azo-Dye | 2.5 | 4 | 75 | 3 | 81.9 | Pure TTA | 2.8 Assay 91.3 N-Oxide 2.4 |
| Azo-Dye | 2.5 | 4 | 78 | 3 | 78.0 | — | — |
| Azo-Dye | 2.5 | 4 | 75 | 4 | — | Mixture of TTA and N-Oxide | TTA-54.4 N-Oxide 38.5 |
| Azo-Dye | 1.5 | 4 | 75 | 3 | 79.1 | Pure TTA | — |
| Azo-Dye | 1 | 4 | 72–75 | 2 | — | Mixture | — |
| Azo-Dye | 1 | 4 | 75 | 3 | 62.6 | Contaminated by N-Oxide | — |
| Azo-Dye | 1 | 4 | 75 | 4 | — | Mixture | — |
| Azo-Dye (a) | 2.5 | 4 | 74–76 | 3 | 84.3 | Pure TTA | Assay 95.8 |
| Azo-Dye (a) | 2.5 | 4 | 74–78 | 3 | 89.0 | Pure TTA | Assay 97.0 |
| Azo-Dye (a) | 2.5 | 4 | 74–78 | 3 | 87.4 | Pure TTA | — |
| Azo-Dye (a) | 2.5 | 4 | 75–78 | 3 | 89.6 | Pure TTA | — |
| Azo-Dye (a) | 2.5 | 4 | 75–78 | 3 | 88.5 | — | — |
| Azo-Dye | 2.5 | 4 | 75–76 | 3 | 87.6 | Pure TTA | — |
| Azo-Dye | 2.5 | 4 | 70–72 | 3 | 88.1 | — | Assay 95.1 N-Oxide none |
| Azo-Dye | 2.5 | 4 | 80–82 | 3 | Oilish mess | — | Assay 87.0 N-Oxide none |
| Azo-Dye | 2.5 | 6 | 75–76 | 3 | 90.0 | — | Assay 94.6 N-Oxide none |
| Azo-Dye | 2.5(b) | 4 | 70–75 | 3 | 88.6 | — | Assay 94.7 N-Oxide none |
| Azo-Dye | 2.5 | 3 | 70–76 | 3 | 89.2 | — | Assay 95.0 |
| Azo-Dye | 10 | 3 | 26 | 3 | No Reaction at all | — | — |
| Azo-Dye | 5 | 3 | 45 | 3 | — | N-Oxide only | — |
| Azo-Dye (c) | — | 1 | 70 | 1 | 97.9 | Pure N-Oxide | — |

(a) Scaled-up experiments (10 times usual charge), with variations of reaction mixture volume and amount of solvent.
(b) Fluorenol from Aldrich Co.
(c) The experiment is set up intentionally to get N-Oxide.

One can see that when the reaction is conducted using fluorenol at a reaction temperature of from about 60° C. to about 80° C., the reaction can be brought to substantial completion with a much reduced amount of catalyst and at a much reduced reaction time as compared to the use of ketone catalysts as shown in the following comparative examples.

COMPARATIVE EXAMPLE 1

2-(2′H-Benzotriazol-2′-yl)-4-tert-octylphenol 35.5g (0.1 mole) of 2-nitro-2′-hydroxy-5-t-octylazobenzene are added to the mixture of 60 ml of methanol, 2.3 g of fluorenone and 64 g of 50% aqueous solution of sodium hydroxide. The mixture is stirred at 70°–75° C. and to the mixture is slowly added 55.4 g (0.3 mol) of glucose in 55 ml of water over 2 hours. The reaction mixture is heated for an additional three hours, then 160 ml of methanol is added at 55°–60° C. and 14.2 g of 35% hydrochloric acid slowly added and stirred at 40°–50° C. for 20 minutes. During this time crystals should appear. Then more hydrochloric acid is added to attain pH 4–5. The reaction is cooled to 25° C. to yield 26.5 g (82%). Compared to Example 1, above, more than three times the amount of fluorenone is needed, more than double the reaction time is required, and a lower yield is obtained than when fluorenol is used.

COMPARATIVE EXAMPLE 2

Example 1 from EP 0,257,151 is duplicated. 2-nitro-2′-hydroxy-3′, 5′-di-t-amylazobenzene (12.8 g) is added to a mixture of methanol (41 g), water (10 g) and 97% sodium hydroxide (11 g), and the resultant mixture is stirred at 65° C. for 30 minutes. Thereafter, 9-fluorenone (2.0 g) and then glucose (12 g) are added to the mixture at 60° to 65° C. over 4 hours. The resultant mixture is further stirred for 4 hours at the boiling point (70° C.), thus completing the reduction reaction. Thereafter, water (50 ml) is added to the reaction liquor, and the reaction liquor is neutralized with 62% sulfuric acid (13 g). The liquor thus neutralized is cooled to 20° C. to precipitate a crystal. The crystal thus obtained is separated by filtration, and the separated crystal is fully washed with water and further with methanol. The washed crystal is then dried, thus producing 9.9 g of 2-(2'-hydroxy-3', 5'-di-t-amylphenyl)benzotriazole having a melting point of 77° to 79° C. at the yield of 85.0%. One can see that the reduction reaction with the aromatic ketone 9-fluorenone takes over 8½ hours to complete and requires three times as much catalyst.

COMPARATIVE EXAMPLE 3

Example 5 of EP 0,257,151 is duplicated. Water (70 ml), 97% sodium hydroxide (5.2 g), 2-nitro-2'-hydroxy-5'-methylazobenzene (12.9 g) and toluene (10 ml) are mixed and heated to 60° C. After stirring, hydroquinone (0.6 g) is added, and glucose (5.0 g) is added to the mixture over one hour at 40° to 45° C. The mixture is further stirred two hours, and the azobenzene disappears. The reaction liquor is neutralized with 62% sulfuric acid (5.8 g), and is cooled to 20° C. to precipitate a crystal. The crystal thus precipitated is separated filtration to obtain a wet product 12 g of 2-(2'-hydroxy-5'-methylphenyl)benzotriazole-N-oxide (dry weight 10.8 g, yield: 90.0%, and melting point: 138° to 140° C.).

To the wet product 12 g (~0.4 mol) thus obtained, is added methanol (60 ml), water (30 ml), 97% sodium hydroxide (13.0 g) and 9-fluorenone (0.5 g), and glucose (5.5 g) (0.3 mol) is further added to the mixture over an hour while stirring at 50° to 55° C. The mixture is reacted while stirring at 75° C. (boiling point) for 5 hours. As a result, the N-oxide disappears. The reaction liquor is neutralized with 62% sulfuric acid (19.8 g) to pH 8 to precipitate a crystal. The precipitated crystal is separated by filtration, and the separated crystal is fully washed with water and further with methanol. The washed crystal is then dried, thus obtaining 9.4 g of 2-(2'-hydroxy-methylphenyl) benzotriazole having a melting point of 128 to 130° C. at the yield of 92.8%. One can see that the reduction with aromatic ketones takes over 9 hours to complete. This reduction also required the use of two catalysts and a greater amount of total catalysts.

COMPARATIVE EXAMPLE 4

Example 1 from U.S. Pat. No. 4,835,284 is duplicated. 2-nitro-2'-hydroxy-3',5'-di-t-amylazobenzene (12.8 g) is added to a mixture of methanol (41 g), water (10 g) and 97% sodium hydroxide (11 g), and the resultant mixture is stirred at 65° C. for 30 minutes. Thereafter, 9-fluorenone (2.0 g) and then glucose (12 g) are added to the mixture at 60° C. to 65° C. over 4 hours. The resultant mixture is further stirred for 4 hours at the boiling point (70° C.), thus completing the reduction reaction. Thereafter, water (50 ml) is added to the reaction liquor, and the reaction liquor is neutralized with 62% sulfuric acid (13 g). The liquor thus neutralized is cooled to 20° C. to precipitate a crystal. The crystal thus obtained is separated by filtration, and the separated crystal is fully washed with water and further with methanol. The washed crystal is then dried, thus producing 9.9 g of 2-(2'-hydroxy-3',5'-di-t-amylphenyl)-benzotriazole having a melting point of 77° to 79° C. at the yield of 85.0%. One can see that reduction using the aromatic ketone 9-fluorenone takes over 8½ hours.

COMPARATIVE EXAMPLE 5

Example 4 from U.S. Pat. No. 4,835,284 is duplicated. 97% sodium hydroxide (8.2 g) is added and dissolved in a mixture of methanol (60 ml) and water (20 ml). 2-nitro-4-chloro-2'-hydroxy-3'-t-butyl-5'-methylazobenzene (11.6 g) is then added to the resultant solution at 50° to 60° C. over 30 minutes while stirring, and thereafter 2,3-dichloro-1,4-naphthoquinone (0.3 g) and 9-fluorenone (0.4 g) are added to the solution. Glucose (8 g) is then added to the resultant mixture at 40° to 50° C. over two hours, and the mixture is stirred for one hour at the same temperature. As this result, almost all of the azobenzene disappears to produce 2-(2-hydroxy-3-t-butyl-5-methylphenyl)-5-chlorobenzotriazole-N-oxide. The system is heated, and is stirred at 66° to 68° C. (boiling point) for 5 hours. As this result, the N-oxide disappears. Thereafter, water (50 ml) is added to the reaction liquor, and the resultant reaction liquor is neutralized with 62% sulfuric acid (10 g) to precipitate a crystal. The precipitated crystal is separated by filtration, and the separated crystal is fully washed with hot water of 60° to 70° C. and further with a small amount of methanol. The washed crystal is then dried, thus obtaining 8.7 g of 2-(2'-hydroxy-3'-t-butyl-5'-methylphenyl)-5-chlorobenzotriazole having a melting point of 138° to 140° C. at the yield of 82.9%. One can see that the reaction using an aromatic ketone takes over 7½ hours.

COMPARATIVE EXAMPLE 6

Example 5 of U.S. Pat. No. 4,835,284 is duplicated. Water (70 ml), 97% sodium hydroxide 5.2 g, 2-nitro-2'-hydroxy-5'-methylazobenzene (12.9 g) and toluene (10 ml) are mixed and heated to 60° C. After stirring, hydroquinone (0.6 g) is added and glucose (5.0 g) is added to the mixture over one hour at 40° to 45° C. The mixture is further stirred for two hours, and the azobenzene disappears. The reaction liquor is neutralized with 62% sulfuric acid 5.8 g, and is cooled to 20° C. to precipitate a crystal. The crystal thus precipitated is separated by filtration to obtain a wet product 12 g of 2-(2'-hydroxy-5'-methylphenyl)benzotriazole-N-oxide (dry weight: 10.8 g, yield 90.0%, and melting point: 138° C. to 140° C.). To the wet product (12 g) thus obtained, are added methanol (60 ml), water (30 ml), 97% sodium hydroxide (13.0 g) and 9-fluorenone (0.5 g), and glucose (5.5 g) is further added to the mixture over one hour while stirring at 50° to 55° C. The mixture is reacted while stirring at 75° C. (boiling point) for 5 hours. As a result, the N-oxide disappears. The reaction liquor is neutralized with 62% sulfuric acid 19.8 g to pH 8 to precipitate a crystal. The precipitated crystal is separated by filtration, and the separated crystal is fully washed with water and further with methanol. The washed crystal is then dried, thus obtaining 9.4 g of 2-(2'-hydroxy-5'-methylphenyl)benzotriazole having a melting point of 128° to 130° C. at the yield of 92.8%. One can see that the reaction using an aromatic ketone takes over 9 hours to complete. Two catalysts are also required.

COMPARATIVE EXAMPLE 7

Example 7 of U.S. Pat. No. 4,835,284 is duplicated. 97% sodium hydroxide (14.4 g) is added to a mixture of methanol (72 ml) and water (36 ml). 2-nitro-2'-hydroxy- 5'-t-butylazobenzene (15.0 g) is then added to the resultant mixture and the mixture is heated to 45°-5020 C. Hydroquinone (0.4 g) and then glucose (5.0 g) are added to the heated mixture over 30 minutes while stirring. The mixture is further stirred for one hour. As this result, the azobenzene disappears to produce 2-(2'-hydroxy-5'-t-butylphenyl)benzotriazole-N-oxide. 9-fluorenone (0.7 g) is then added to the reaction liquor thus obtained, and the liquor is heated to 55°-60° C. Thereafter, glucose (6.0 g) is added to the reaction liquor over 30 minutes, and the reaction is conducted at 75° C. (boiling point) for 6 hours. As a result, the N-oxide disappears. Thereafter, the pH of the reaction liquor is brought to 8 with 62% sulfuric acid (19.0 g) to precipitate a crystal. The precipitated crystal is separated by filtration, and the separated crystal is fully washed with water and further with methanol. The washed crystal is then dried, thus obtaining 11.6 g of 2-(2'-hydroxy-5'-t-butylphenyl)benzotriazole. One can see that the reaction using an aromatic ketone takes over 8 hours to complete. Two catalysts are also required.

COMPARATIVE EXAMPLE 8

Example 9 of U.S. Pat. No. 4,835,284 is duplicated. A mixture of methanol (60 ml), water (30 ml), 97% sodium hydroxide (12.4 g), and 2-nitro-2'-hydroxy-5'-methyl azobenzene (12.9 g) is heated and stirred at 45°-50° C. 9-Fluorenone (1.0 g) and then glucose (5.5 g) are added to the resultant mixture over 30 minutes while stirring. The mixture is further stirred at 75° C. (boiling point) for 7 hours. As a result, the azobenzene disappears to produce 2-(2'-hydroxy-5'-methylphenyl)benzotriazole-N-oxide. Glucose (6 g) is then added to the reaction liquor over 30 minutes and the reaction is conducted 75° C. (boiling point) for further 6 hours. As a result, the above prepared N-oxide disappears. Thereafter, water (50 ml) is added to the reaction liquor, and the resultant reaction liquor is neutralized with 62% sulfuric acid (15 g) to precipitate a crystal. The precipitated crystal is separated by filtration, and the separated crystal is fully washed with water and further with methanol. The washed crystal is then dried, thus obtaining 9.6 g of 2-(2'-hydroxy-5'-methylphenyl)benzotriazole having a melting point of 128° to 130° C. at the yield of 85.0%. One can see that the reaction using the aromatic ketone 9-fluorenone takes over 14 hours to complete.

COMPARATIVE EXAMPLE 9

Example 11 of U.S. Pat. No. 4,780,541 is duplicated. This is an example of the use of an aldehyde reducing agent and the aromatic ketone 9-fluorenone as a catalyst. Methanol (110 ml), water (20 ml), 97% sodium hydroxide (12.4 g), and 2-nitro-2'-hydroxy-5'-t-octylazobenzene (17.8 g) are mixed and stirred. After adding 9-fluorenone (2.4 g) to the resultant mixture at 65° to 70° C., 80% paraformaldehyde (6 g) is added to the mixture for 4 hours, and then the reaction liquor is further stirred at the boiling point (73° C. ) for 6 hours, thus the reduction reaction having completed. Thereafter, water (50 ml) is added to the reaction liquor, and the reaction liquor is neutralized to pH 8 with 62% sulfuric acid (16 g) to precipitate a crystal. The crystal thus obtained is filtered by suction to separate the crystal, and the separated crystal is fully washed with water and further with methanol. The washed crystal is then dried, thus producing 13.1 g of 2-(2-hydroxy-5-t-octylphenyl)benzotriazole having a melting point of 103° to 105° C. at the yield of 81.0%. One can see that the reaction takes over 10 hours to complete.

What is claimed is:

1. A method for the production of 2-aryl-2H-benzotriazoles having the general formula:

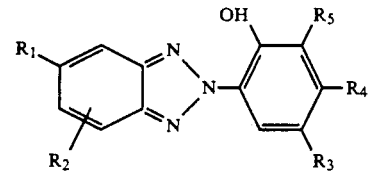

which comprises reducing an o-nitroazobenzene compound having the general formula:

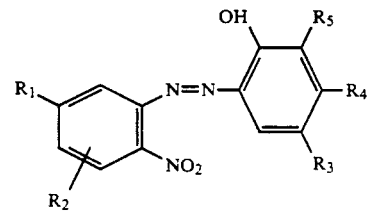

wherein $R_1$ is a hydrogen or chlorine atom, a lower alkyl group having a carbon number of 1 to 4, a lower alkoxyl group having a carbon number of 1 to 4, a carboxyl group, or a sulfonic acid group; $R_2$ is a hydrogen or chlorine atom, a lower alkyl group having a carbon number of 2 to 4, or a lower alkoxyl group having a carbon number of 1 to 4; $R_3$ is a hydrogen or a halogen atom, an alkyl group having a carbon number of 1 to 12, a lower alkoxyl group having a carbon number of 1 to 4, a phenyl group, a phenyl group substituted with an alkyl group having a carbon number of 1 to 8, a phenoxy group, or a phenylalkyl group, the alkyl part of which has a carbon number of 1 to 4; $R_4$ is a hydrogen or chlorine atom, a hydroxyl group, or a lower alkoxyl group having a carbon number of 1 to 4; and $R_5$ is a hydrogen atom, an alkyl group having a carbon number of 1 to 12, or a phenylalkyl group, the alkyl part of which has a carbon umber of 1 to 4; with a saccharide having an aldehyde group as a reducing agent, in the presence of fluorenol as a catalyst, and a base in an aqueous alcoholic solution, at a temperature of from 60° C. to about 80° C., for a sufficient time and under conditions sufficient to produce the 2-aryl-2H-benzotriazole.

2. The method of claim 1 wherein the saccharide having an aldehyde group is selected from the group consisting of glucose, fructose, sucrose, lactose and maltose.

3. The method of claim 1 wherein the base is selected from the group consisting of alkali metal and alkaline earth metal hydroxides.

4. The method of claim 1 wherein the lower alkyl alcohol is selected from the group consisting of water miscible $C_1$ to $C_4$ alcohols.

5. The method of claim 1 wherein the o-nitroazobenzene has the formula

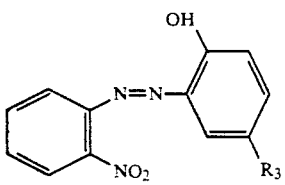

wherein $R_3$ is selected from the group consisting of $C_1$–$C_{12}$ alkyl or halogen.

6. The method of claim 1 wherein $R_3$ is methyl or chlorine.

7. The method of claim 1 wherein the o-nitroazobenzene is 2-nitro-2'-hydroxy-5-t-octylazobenzene.

8. The method of claim 1 wherein the saccharide is glucose.

9. The method of claim 1 wherein the amount of fluorenol is present in the reaction is from about 1.5% to about 10% based on the weight of the o-nitroazobenzene.

10. The method of claim 1 wherein the amount of fluorenol present in the reaction is from about 2% to about 2.5% based on the weight of the o-nitroazobenzene.

11. The method of claim 8 wherein the amount of fluorenol present in the reaction is from about 1.5% to about 10% based on the weight of the o-nitroazobenzene.

12. The method of claim 1 wherein the amount of saccharide present in the reaction is from at least about 2 mols to about 4 moles based on the molar amount of o-nitroazobenzene.

13. The method of claim 8 wherein the amount of glucose present in the reaction is from at least about 2 mols to about 4 mols based on the molar amount of o-nitroazobenzene.

14. The method of claim 1 wherein the reduction is conducted for from about 2 hours to about 6 hours.

15. The method of claim 1 wherein the reduction is conducted at a temperature of from about 70° C. to about 75° C.

16. The method of claim 1 wherein the reduction is conducted in a medium which is an aqueous solution of methanol.

17. The method of claim 1 wherein the o-nitroazobenzene is 2-nitro-2'-hydroxy-5-t-octylazobenzene, the saccharide is glucose, the base is a sodium or potassium hydroxide, the amount of fluorenol present in the reaction is from about 2% to about 2.5% based on the weight of the o-nitroazobenzene; wherein the amount of glucose present in the reaction is from about 2 mols to about 4 mols based on the molar amount of o-nitroazobenzene, wherein the reduction is conducted for from about 2 hours to about 6 hours, wherein the reduction is conducted at a temperature of from about 70° C. to about 75° C., and the reaction medium is an aqueous solution of methanol.

18. A method for the production of 2-aryl-2H-benzotriazoles having the general formula:

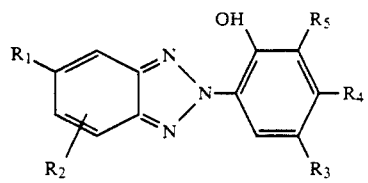

which comprises reducing a 2-aryl-2H-benzotriazole-N-oxide compound having the general formula:

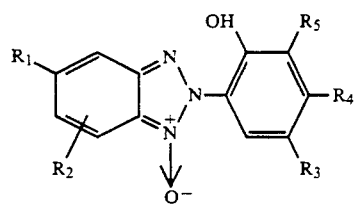

wherein $R_1$ is a hydrogen or chlorine atom, a lower alkyl group having a carbon number of 1 to 4, a lower alkoxyl group having a carbon number of 1 to 4, a carboxyl group, or a sulfonic acid group; $R_2$ is a hydrogen or chlorine atom, a lower alkyl group having a carbon number of 1 to 4, or a lower alkoxyl group having a carbon number of 1 to 4; $R_3$ is a hydrogen or a halogen atom, an alkyl group having a carbon number of 1 to 12, a lower alkoxyl group having a carbon number of 1 to 4, a phenyl group, a phenyl group substituted with an alkyl group having a carbon number of 1 to 8, a phenoxy group, or a phenylalkyl group, the alkyl part of which has a carbon number of 2 to 4; $R_4$ is a hydrogen or chlorine atom, a hydroxyl group, or a lower alkoxyl group having a carbon number of 1 to 4; and $R_5$ is a hydrogen atom, an alkyl group having a carbon number of 1 to 12, or a phenylalkyl group, the alkyl part of which has a carbon umber of 1 to 4; with a saccharide having an aldehyde group as a reducing agent, in the presence of fluorenol as a catalyst, and a base in an aqueous alcoholic solution, at a temperature of from about 60° C. to about 80° C., for a sufficient time and under conditions sufficient to produce the 2-aryl-2H-benzotriazole.

19. The method of claim 18 wherein the saccharide is selected from the group consisting of glucose, fructose, sucrose, lactose and maltose.

20. The method of claim 18 wherein the base is selected from the group consisting of alkali metal and alkaline earth metal hydroxides.

21. The method of claim 18 wherein the lower alkyl alcohol is selected from the group consisting of water miscible $C_1$ to $C_4$ alcohols.

22. The method of claim 18 wherein the N-oxide has the formula

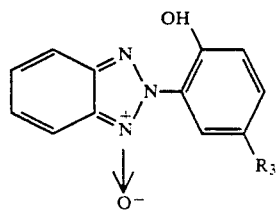

wherein $R_3$ is selected from the group consisting of $C_1$–$C_{12}$ alkyl or halogen.

* * * * *